(12) United States Patent
Yaldo

(10) Patent No.: US 7,374,562 B2
(45) Date of Patent: May 20, 2008

(54) METHOD AND SYSTEM FOR CONDUCTIVE KERATOPLASTY

(76) Inventor: Mazin K. Yaldo, 4754 Old Orchard Trail, Orchard Lake, MI (US) 48324

( * ) Notice: Subject to any disclaimer, the term of this patent is extended or adjusted under 35 U.S.C. 154(b) by 0 days.

(21) Appl. No.: 11/161,747

(22) Filed: Aug. 15, 2005

(65) Prior Publication Data

US 2007/0038211 A1    Feb. 15, 2007

(51) Int. Cl.
*A61B 18/18* (2006.01)
(52) U.S. Cl. .............................. 606/41; 606/4; 606/29; 606/170; 607/98; 607/101; 128/898
(58) Field of Classification Search ................ 606/166, 606/167, 168, 169, 170, 177, 32, 41, 4, 5, 606/27–29, 40; 607/96, 98, 101; 128/898
See application file for complete search history.

(56) References Cited

U.S. PATENT DOCUMENTS

| | | | |
|---|---|---|---|
| 5,533,999 A | 7/1996 | Hood | |
| 5,634,921 A | 6/1997 | Hood | |
| 5,749,871 A | 5/1998 | Hood | |
| 6,213,997 B1* | 4/2001 | Hood et al. ..................... | 606/5 |
| 2005/0197657 A1* | 9/2005 | Goth et al. .................. | 606/41 |
| 2005/0203554 A1* | 9/2005 | Dykes ........................ | 606/166 |
| 2005/0245948 A1* | 11/2005 | Khalaj ........................ | 606/166 |
| 2005/0245949 A1* | 11/2005 | Goth et al. ................. | 606/166 |
| 2007/0038210 A1* | 2/2007 | Yaldo ........................ | 606/41 |
| 2007/0038234 A1* | 2/2007 | Yaldo ........................ | 606/166 |
| 2007/0038276 A1* | 2/2007 | Yaldo ........................ | 607/96 |
| 2007/0106376 A1* | 5/2007 | Roberts et al. ............. | 623/4.1 |

FOREIGN PATENT DOCUMENTS

| | | |
|---|---|---|
| AU | 691198 | 5/1998 |
| AU | 199880769 | 10/1998 |
| AU | 714774 | 1/2000 |
| AU | 200118269 | 5/2001 |

\* cited by examiner

*Primary Examiner*—Ahmed M Farah
(74) *Attorney, Agent, or Firm*—John A. Artz; Dickinson Wright PLLC

(57) ABSTRACT

Improved corrective procedures for conductive keratoplasty are disclosed. Over correction can be relieved by the addition of one or two spots along one of the rings on the cornea.

12 Claims, 3 Drawing Sheets

METHOD AND SYSTEM FOR CONDUCTIVE KERATOPLASTY

CROSS-REFERENCE TO RELATED APPLICATIONS

This application is related to U.S. patent applications Ser. No. 11/163,340 entitled "Instrumentation for Conductive Keratoplasty" and U.S. Ser. No. 11/161,746 entitled "Method and System for Conductive Keratoplasty", both of which were filed on the same day as the present application, and the disclosures of which are hereby incorporated by reference herein.

TECHNICAL FIELD

The present invention relates to improvement in conductive keratoplasty (CK), and more particularly to improvements in CK instruments, treatment procedures, and post-operative procedures.

BACKGROUND OF THE INVENTION

Eyeglasses and contact lenses can be inconvenient for many people. Some people are unhappy with the restrictions that corrective lenses put on their lives and lifestyles. Glasses and contact lenses can interfere with sports like swimming and golf, and can even disqualify people from certain professions. Also, some people cannot wear contact lenses successfully, while many people do not like the way they look in glasses or the way glasses make them feel about themselves.

Due to medical advances in vision correction techniques, people today can reduce their dependence on glasses and contacts. Vision correction techniques today include Lasik procedures, Lasek procedures, radiokeratomy (RK), conduct keratoplasty (CK) and the like. Numerous persons have found that they are viable candidates for one of these procedures and have had their vision successfully corrected and/or improved.

Conductive keratoplasty ("CK") uses radio frequency energy instead of a laser to reshape the contours of an eye. CK procedures change the way the cornea directs light to the eye and effectively reduces the need for reading glasses.

There is a need today for improved instruments and procedures for performing conductive keratoplasty, particularly for persons with cornea thickness outside of conventional ranges. There is also a need for improved procedures and techniques for enhancing the results of CK operations where necessary.

SUMMARY OF THE INVENTION

The present invention provides improved instruments for performing conductive keratoplasty (CK) operations, as well as improved methods for performing such operations, as well as improved methods and techniques for providing corrective and/or enhancement surgery in post-operative conditions.

The keratoplast tips commonly used with CK operations have a predetermined length and produces satisfactory results for most patients. With many patients, typically those with thick corneas, CK procedures provide results having limited duration.

With the present invention, elongated tips, and tips with predetermined steps or stops, are provided which allow improved CK procedures, particularly with patients having thick corneas. Kits of probes of different lengths can be provided.

In addition, CK procedures are improved by the addition of providing more sites at different positions on the cornea for treatment. This compensates in part for the use of conventional keratoplast tips, but also can be used with the improved tips in accordance with the present invention.

In the instances where there is an over response to the cornea following CK procedures, the tightness can be relieved by the addition of one or two more spots of CK applications at various positions on the cornea where astigmatism is present. The reduction of astigmatism reduces the tightness and therefore the over response, which can bring the patient's vision to the appropriate level.

These and other objects, features, and benefits of the present invention will become apparent from the following description of the invention when viewed in accordance with the accompanying drawings and appended claims.

DESCRIPTION OF PREFERRED EMBODIMENTS

Figure 1:
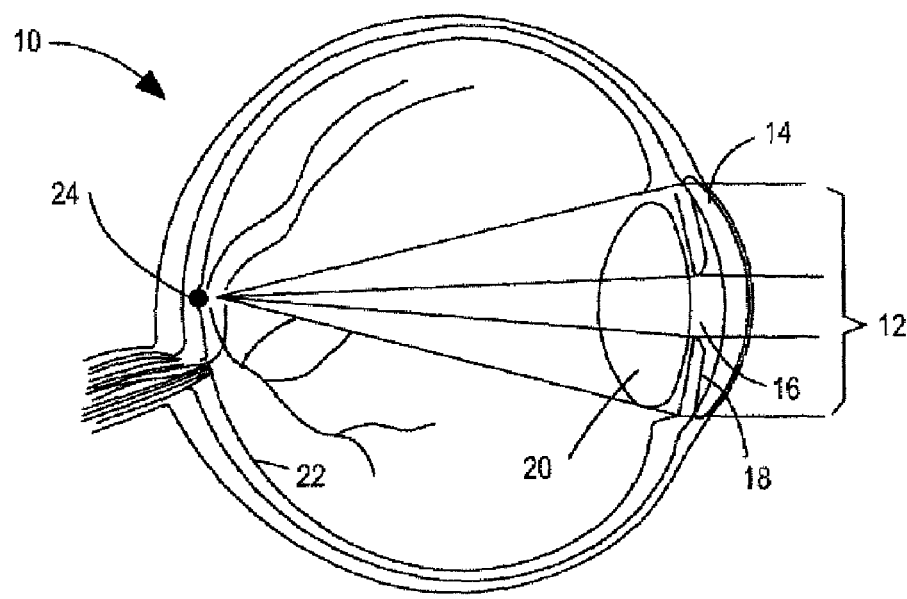
FIG. 1 is a schematic representation of a human eye.

FIG. 1 is a schematic illustration of a human eye. The eye is referred to generally by the reference numeral 10. Light rays 12 enter the eye through the cornea 14 where the light is initially focused. The light then passes through the pupil 16 which is the opening in the center of the eye while the iris 18 works to adjust the amount of light allowed to be entered. Immediately behind the iris is the main lens 20 of the eye which further acts to focus the light rays entering the eye. The shape of the lens 20 can adjust, either thicker or thinner, by tensing or relaxing the muscles of the eye. The light itself is then focused on the retina 22, particularly at the focal point 24. The light is converted into an electrical signal using cells called rods and cones on the retina. The signals travel to the human's brain where they are developed into an image.

Not all human eyes, however, have a perfect shape as shown in FIG. 1 in which the light rays entering the eye are focused precisely on the retina. Myopia, also known as nearsightedness, is a condition where the light rays focus on a point in front of the retina. Vision is best close up. However, distance and often mid-range vision is blurred. Hyperopia, also known as farsightedness, is a condition where the light rays focus at a point behind the retina.

Although such vision is best at a distance, it is usually not good at any single focal point. Also, with hyperopia, both distance and close vision can be blurred.

There are other common conditions, such as astigmatism and presbyopia. Astigmatism relates to irregularly shaped corneas which cause light rays to be focused at different points inside the retina, i.e. in front of the retina, or behind the retina. The result is blurry vision both near and distant. With astigmatism, the person may also have distorted vision, double vision, halos or glare. Presbyopia affects most people over 40 years of age and is part of the natural aging process. The natural crystalline lens 20 of the eye begins to lose its natural flexibility and thus looses its ability to switch between seeing objects at a distance to seeing objects that are close to the eye.

Conductive keratoplasty ("CK") is a corrective vision procedure which is specifically approved for patients with hyperopia and presbyopia. The procedure uses radio frequency energy instead of a laser to reshape the contours of the eye. By changing the way the cornea directs light to the rest of the eye, CK effectively reduces the need for reading glasses.

CK is an effective, minimally invasive procedure for patients, particularly those of low to moderate hyperopia and presbyopia. By a controlled release of radio frequent energy at a preselected plurality of locations, the cornea is gently reshaped. A keratoplasty tip attached to a probe is inserted into the cornea at appropriate spots or sites. The tip utilizes radio frequency energy to increase the temperature of the cornea tissue immediately adjacent the tip. The probe releases controlled high-frequency radio wave energy (350 kHz), and the impedance, or electrical resistance, of the corneal collagen causes it to heat up in response. The heating causes the collagen to shrink in a predictable manner.

The resulting shrinkage produces an effect comparable to tightening a belt around the cornea, causing the cornea to be raised up or steepened centrally. The band of tightening results in a slight bulging of the central cornea and flattening of the peripheral cornea.

In order to accurately determine where the spots are to be positioned, the patient is first examined to determine the extent of the correction needed and thus the amount of spots needed to be made in the cornea. During traditional CK procedures, eight to thirty-two treatment spots can be utilized depending on the amount of vision correction needed.

Figure 2:
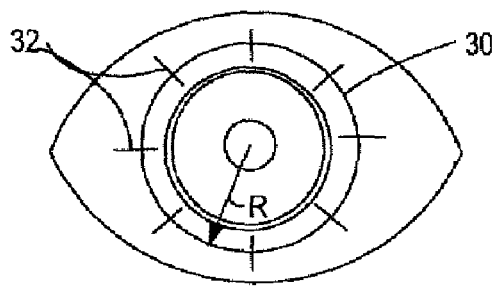
FIG. 2 depicts a front view of an eye which has been marked for corrective CK procedures.

The location and number of spots is determining by a nomogram procedure. This procedure marks a ring 30 on the cornea of the eye, together with eight small hash lines 32 positioned uniformly around the circumference of the ring 30 at eight equal locations. The ring 30 has a radius R from the center of the eye of 7 mm and each of the small hash lines 32 are 2 mm in length. Thus, the inner ends of the hash marks 32 provide a locus of a circle having a radius of 6 mm, while the outer ends of the hash marks 32 provide a ring having a radius of 8 mm. Nomogram marking, including the ring and eight hash marks as shown in FIG. 2, are applied in a conventional manner to the outer surface of the cornea of the eye as part of conventional CK procedure.

Figure 3A:
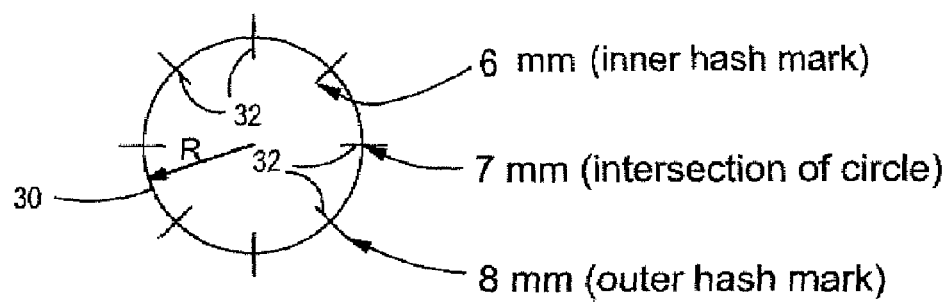
FIG. 3 illustrates conventional locations for CK procedures.
Figure 3B:
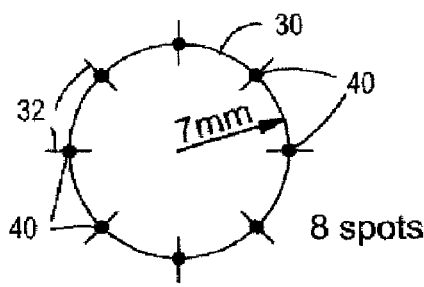
Figure 3C:
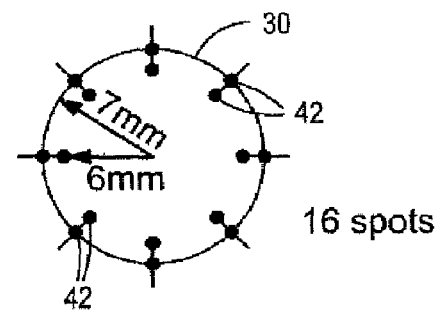

FIG. 3A illustrates schematically one of the nomogram circles 30 with the eight hash marks 32. When the CK procedure only requires eight spots be utilized in correcting the vision of the patient, the keratoplast tip is inserted in eight spots or sites 40 as shown in FIG. 3B. These spots are positioned precisely on the 7 mm ring. In conventional CK procedures where 16 spots are to be utilized, the 16 spots 42 are positioned as shown in FIG. 3C. The 16 spots are positioned in pairs on each of the hash marks, one ring of eight spots at the 7 mm circle and one ring of eight spots at the 6 mm circle.

Figure 3D:
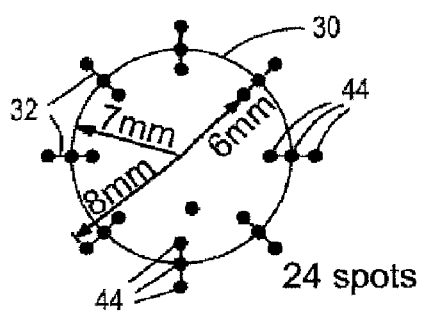
Figure 3E:
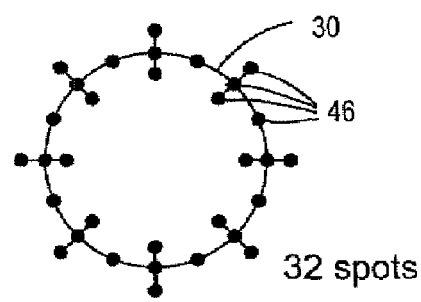

When 24 spots are required to correct a patient's vision, the 24 spots 44 are positioned as shown in FIG. 3D. The spots essentially form three rings on the cornea. The circles have radii of 6, 7 and 8 mm. If it is necessary to utilize 32 spots in order to correct the patient's vision, the 32 spots 46 are positioned as shown in FIG. 3E.

A conventional keratoplastic probe has a tip 450 microns long and is about 90% as wide as a human hair. A conventional tip of this type is provided by Refractec, Inc. in Irvine, Calif., as Model No. VPT-KPT-450.

It has been found that with patients having thick corneas, the duration of the results of the CK procedure may vary and require augmentation or an additional operation. In this regard, preferably the spots made by the keratoplast tip should be inserted into the cornea approximately 80-95% (preferably 85-90%) of the thickness of the cornea. Thus, with a keratoplast tip 450 microns in length, the tip has an effective range for a cornea measuring 500-550 microns in thickness. It has been found, however, that measurements of patients' corneas with an Orb scan procedure often have a thickness greater than 600 microns and sometimes up to 700 or more microns.

Figure 4:
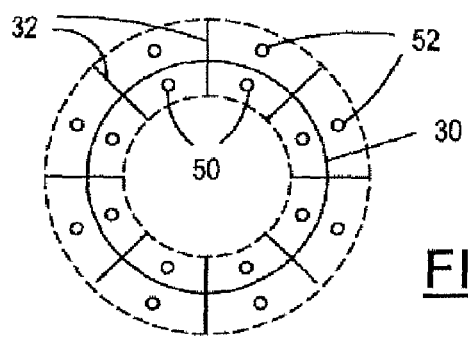
FIG. 4 illustrates CK treatment positions in accordance with the present invention.

In order to provide a CK procedure having a longer duration than the duration of a CK procedure on a thicker cornea using a conventional keratoplastic tip 450 microns in length, one method in accordance with the present invention provides rings of spots at radii of 6 mm, 6.5 mm, 7 mm, 7.5 mm and 8 mm as opposed to the conventional rings of spots at the 6, 7 and 8 mm locations. The rings are positioned depending on the thickness of the cornea. It is also possible in accordance with the present invention in order to provide a longer lasting procedure where the patient has thicker corneas, to add additional spots at the 6.5 mm and 7.5 mm locations in combination with the conventional rings of spots at the 6, 7 and/or 8 mm locations. The latter procedure is depicted in FIG. 4 where the additional spots at the 6.5 mm and 7.5 mm locations are indicated by the reference numerals 50 and 52, respectively. The number of additional spots 50 and 52 and the total number of spots is dependent on the thickness of the cornea and the amount of correction needed. The thicker the cornea, the larger the number of spots that will be needed, and the more centrally located they should be (i.e. the closer to the center of the cornea). Also, the number of spots should increase based on the amount of correction desired by both the doctor and the patient.

Figure 5:
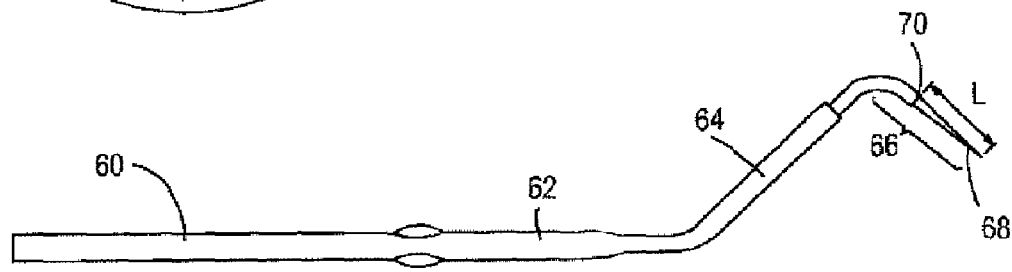
FIG. 5 illustrates a keratoplast tip provided in accordance with the present invention.

A preferred keratoplast probe 60 is shown in FIG. 5. The probe 60 has an elongated support member 62, an angled connection member 64 and an elongated tip member 66 at the distal end. The narrow pointed tip 68 has a length "L" which is greater than 450 microns and is preferably 500 microns or more. The tip 60 has a shoulder or stop 70 which aids the surgeon in inserting the tip member 68 the requisite depth into the cornea.

Figure 6:
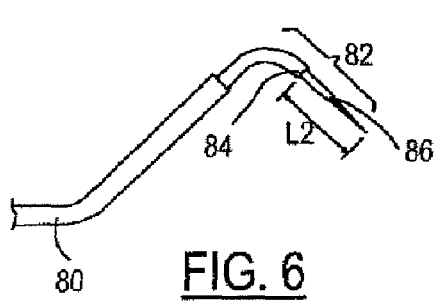
FIG. 6 illustrates an alternate embodiment of a keratoplast tip in accordance with the present invention.

Another embodiment of a keratoplast tip in accordance with the present invention is shown in FIG. 6. The tip 80 has an elongated probe member 82 which has two stop members 84 and 86 along its length. The overall length "L2" from the first stop 84 to the distal end of the tip is again at least 500 microns in length.

In accordance with one embodiment of the present invention, a sensor kit of keratoplast probes are provided, each with a different length tip. As indicated above, the corneas of patients have different thicknesses and can range from under 500 microns to over 700 microns. In addition, the thickness of a cornea on a patient's eye is typically not uniform throughout but can have a variation in thickness from the center to the perimeter. It has been determined for optimum results of a keratoplast procedure, that the depth of the spots should be on the order of 80-95% and preferably 85-90% of the thickness of the cornea. Thus, with a conventional keratoplast tip of 450 microns, the tip has optimum results with corneas in the range of 500-525 microns.

With the present invention, a series of keratoplast probes—preferably five—are provided as follows:

| Tip Length (Microns) | Cornea Thickness (Microns) | % Depth |
|---|---|---|
| 450 | 500-550 | 81-90% |
| 500 | 551-600 | 83-91% |
| 550 | 601-650 | 84-91% |
| 600 | 651-700 | 86-92% |
| 650 | 701-750 | 86-93% |

In this manner, once the thickness of the patient's corneas are determined, the surgeon can select the appropriate tip (or probe which has the appropriate length tip) in order for the pots to be formed at the appropriate depth. With all of the spots having a depth on the order of 80-95% of the thickness of the cornea, the keratoplast procedure should have longer duration.

Figure 8:
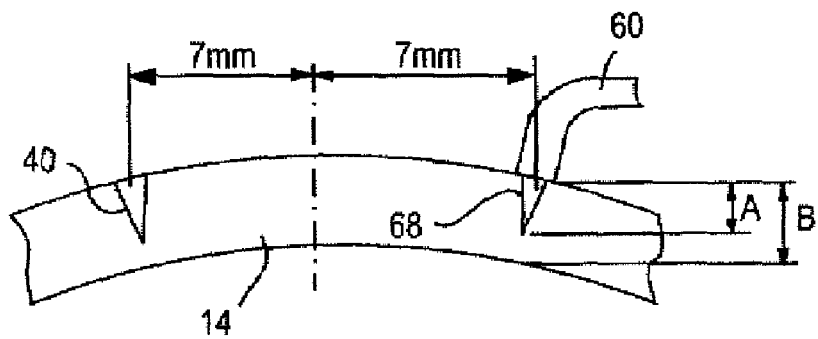
FIG. 8 is a cross-section of a cornea illustrating the formation of a spot.

FIG. 8 schematically illustrates the use of a keratoplast probe and formation of a spot. The tip 68 of the probe 60 is inserted into the cornea 14 to a depth A, which is approximately 80-95% of the thickness B of the cornea. The tip of the probe will form a spot similar to spot 40 which is illustrated as having been formed by the probe on the 7 mm ring. The tip 68 should be precisely placed at the desired locations and perpendicular to the surface of the cornea. The tip is applied individually and separately to make all of the desired numbers of spots (8, 10, 24, 32, etc.). A gentle uniform pressure applied by the surgeon seats the tip into the cornea at each location and forms the spots.

Figure 9:
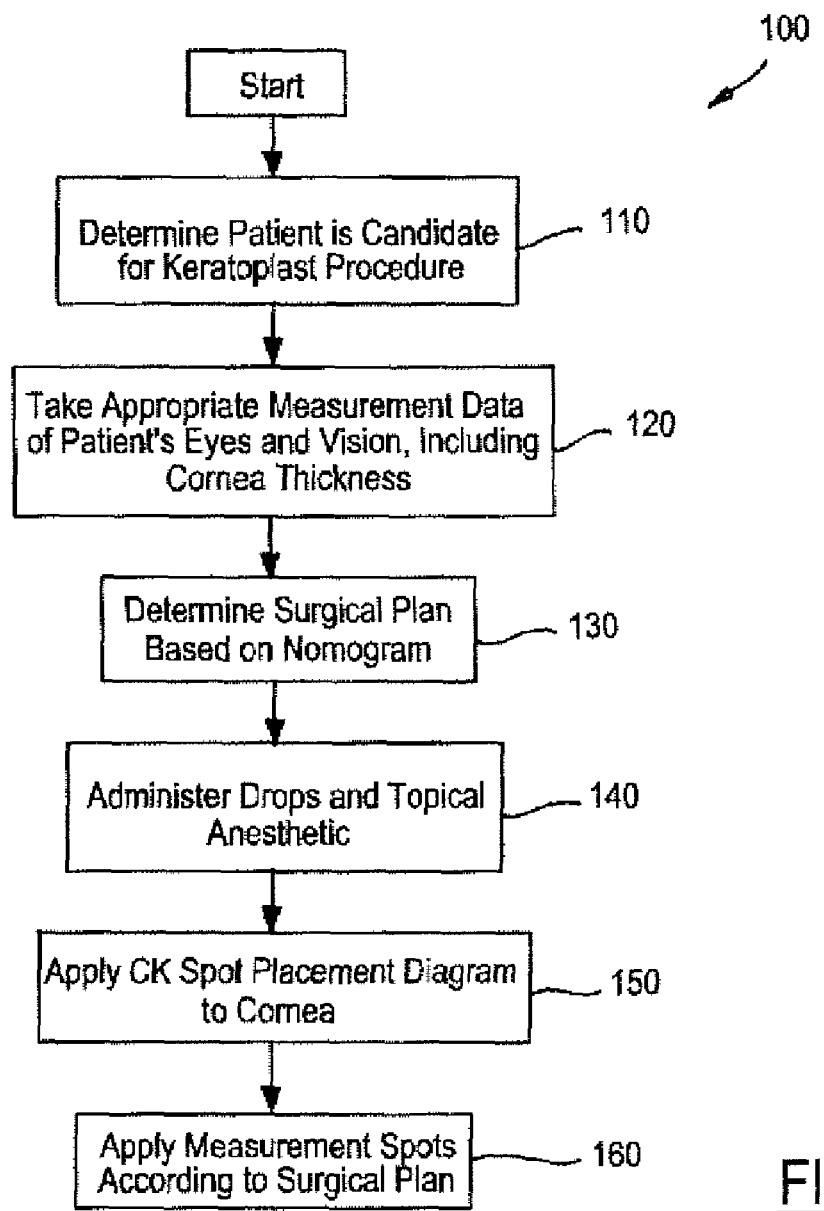
FIG. 9 is a flow diagram illustrating a CK procedure in accordance with the present invention.

FIG. 9 is a flow diagram 100 which sets forth the basic procedures of a CK procedure in accordance with the present invention. First, once a determination has been made that the patient is a viable candidate for the CK procedure 110, appropriate tests and measurements are made of the patient's vision and eyes, including the thickness of the cornea 120. A surgical plan based on the nomogram is formed 130 and the patient is prepared and prepared for the operation 140. The spot placement pattern is then provided on the patient's cornea 150. Thereafter, the surgeon then applies the desired number of CK spots 160 on the cornea.

As indicated above, CK procedures create a tight band on the cornea which gently changes the curvature of the cornea and thus corrects the patient's vision. However, the corrective procedure at times can create an over correction which can distort the patient's vision and which needs to be corrected. In these instances, it is necessary to relieve some of the tightening and bring the patient's vision into a more acceptable level.

Figure 7:
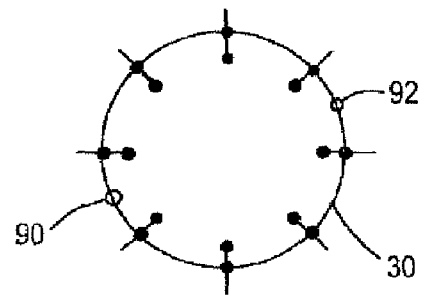
FIG. 7 is a schematic illustration illustrating the use of corrective spots to eliminate or reduce tightening of the cornea following a CK operation.

In this regard, it has been found in accordance with the present invention that the tightening of the band around the cornea after a CK procedure can be relieved by adding one or two more spots on the cornea at different locations on one of the rings. This is shown in FIG. 7. The additional spot 90 is positioned 90° away from the greatest amount of astigmatism as measured in plus cylinder format. The reduction of astigmatism reduces the tightness of the cornea and brings the patient's vision back to the levels desired. The actual position of the additional spot 90, i.e. whether on the 6 mm, 7 mm or 8 mm ring, will depend on the thickness of the cornea. The thicker the cornea, the closer to the center of the cornea the spot should be positioned. If the correction is relatively minor (i.e. one diopter or less), only one spot 90 is needed in order to adjust the tension and correct the vision. However, if more correction is needed, such as two diopters or more, then two spots 90 and 92 can be utilized. Where two spots are utilized, they typically are placed 180° apart, as shown in FIG. 7. Again, the actual positioning of the two spots is dependent on the curvature of the cornea following the CK procedure. Also, the location of the spots, i.e. whether on the 6, 7, or 8 mm rings, will depend on the thickness of the cornea.

It is also possible to use the improved method wherein certain spots are positioned at the 6.5 and 7.5 mm radius rings (as well as the 6, 7 and 8 mm rings), together with the new probe, which has a longer pointed tip of 500 microns. This may depend on the thickness of the patient's cornea. Upon examination prior to the operation, if the cornea thickness is at the high end of the range, that is 680-700 microns in thickness, then the use of the inventive procedure with the new inventive tip may be appropriate.

While various embodiments of the invention have been shown and described, numerous variations and alternate embodiments will occur to those skilled in the art. Accordingly, it is intended that the invention be limited only in terms of the appended claims.

What is claimed is:

1. A method for relieving over correction on a patient's cornea subsequent to an initial conductive keratoplasty (CK) procedure on the cornea, said method comprising the steps of:
   (a) measuring the amount and location of spots needed to secure the desired result of the corrective CK procedure, said amount of said spots being one or two;
   (b) determining the amount and location of said corrective CK spots needed to secure the desired result of the initial CK procedure; and
   (c) performing the corrective CK procedure by making said one or two spots on the patient's cornea at the desired location and distance from the center of the eye.

2. The method for relieving over correction of an initial conductive keratoplasty (CK) procedure as described in claim 1 wherein two spots are provided and said two spots are positioned 180° apart.

3. The method for relieving over correction of an initial conductive keratoplasty (CK) procedure as described in claim 1 wherein the over correction is one diopter or less and one spot is made on the patient's cornea.

4. The method for relieving over correction of an initial conductive keratoplasty (CK) procedure as described in claim 1 wherein the over correction is two diopters or more and two spots are made on the patient's cornea.

5. A method for relieving over correction of an initial conductive keratoplasty (CK) procedure on a cornea of a patient subsequent to a CK procedure on that patient wherein a plurality of CK spots in the range of 8-32 spots have been made on the cornea and after determining relief is needed, the method comprising the steps of:
   (a) determining the number and location of relief correction spots needed on the patient's cornea, said relief correction spots being either one or two spots; and
   (b) performing said additional spot or spots on the patient's cornea at the determined location.

6. The method as described in claim 5 wherein two additional spots are made on the patient's cornea to relieve the over correction.

7. The method as described in claim 6 wherein two spots are performed and said two spots are spaced substantially 180° apart.

8. The method as described in claim 5 wherein the number of relief correction spots is determined in based on diopters and wherein one additional spot is made for <2 diopters and two additional spots are made for ≧2 diopters.

9. A method of performing conductive keratoplasty (CK) procedure on the cornea of a person's eye, said method comprising the steps of:
  (a) determining the amount and location of spots on the cornea needed to secure the desired result of the CK procedure, the amount of spots being in the range from 8 to 32;
  (b) performing the CK procedure on the cornea by making at least 8 spots on the cornea;
  (c) subsequently determining if any correction to the patient's vision is necessary following the initial CK procedure;
  (d) measuring the amount of spots needed in a second CK procedure to secure the desired correction of the initial CK procedure;
  (e) determining the locations of corrective CK spots needed to secure the desired correction of the initial CK procedure; and
  (f) performing the corrective CK procedure by making spots on the person's cornea at the desired locations, wherein the amount of said spots for said corrective CK procedure is either one or two spots.

10. The method as described in claim 9 wherein two of said spots are provided, said spots being positioned 180° apart.

11. The method as described in claim 9 wherein the location of said spots in step (e) is determined by the amount of diopters measured in step (d).

12. The method as described in claim 11 wherein one additional spot is made for less than two diopters measured and two additional spots are made if the measurement is two diopters or more.

* * * * *